United States Patent
Allen et al.

Patent Number: 6,083,981
Date of Patent: Jul. 4, 2000

[54] SULFONAMIDE SUBSTITUTED ASPARTIC ACID INTERLEUKIN-1β CONVERTING ENZYME INHIBITORS

[75] Inventors: Hamish John Allen, Boylston; Kenneth Dale Brady, Worcester, both of Mass.; William Glen Harter, Chelsea, Mich.; Elizabeth Ann Lunney, Ann Arbor, Mich.; Mark Stephen Plummer, Dexter, Mich.; Tomi Sawyer, Southborough, Mass.; Aurash Shahripour, Ann Arbor, Mich.; Nigel Walker, Dossenheim, Germany

[73] Assignee: Warner-Lambert Company, Morris Plains, N.J.

[21] Appl. No.: 09/284,425

[22] PCT Filed: Oct. 9, 1997

[86] PCT No.: PCT/US97/18406

§ 371 Date: Apr. 9, 1999

§ 102(e) Date: Apr. 9, 1999

[87] PCT Pub. No.: WO98/16504

PCT Pub. Date: Apr. 23, 1998

Related U.S. Application Data

[60] Provisional application No. 60/028,323, Oct. 11, 1996.

[51] Int. Cl.$^7$ .................... A61K 31/341; C07D 307/40
[52] U.S. Cl. .................... 514/471; 549/479; 549/528; 549/562; 549/563; 560/12; 560/13; 562/430
[58] Field of Search ................ 514/528, 562, 514/563, 471; 560/12, 13; 562/430; 549/479

[56] References Cited

U.S. PATENT DOCUMENTS 5,656,627  8/1997  Bemis et al. ............... 514/221

FOREIGN PATENT DOCUMENTS

| | | |
|---|---|---|
| 0 496 378 | 7/1992 | European Pat. Off. . |
| 0 519 748 | 12/1992 | European Pat. Off. . |
| 93/14066 | 7/1993 | WIPO . |
| 95/26958 | 10/1995 | WIPO . |
| 95/33751 | 12/1995 | WIPO . |
| 95/35308 | 12/1995 | WIPO . |
| 97/22619 | 6/1997 | WIPO . |

*Primary Examiner*—Joseph McKane
*Assistant Examiner*—Taofiq A. Solola
*Attorney, Agent, or Firm*—Charles W. Ashbrook

[57] ABSTRACT

The present invention relates to compounds that are inhibitors of interleukin-1β converting enzyme that have the Formula I, II, or III.

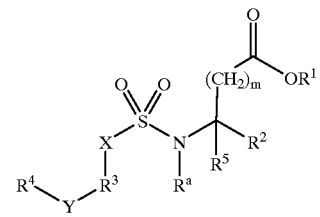

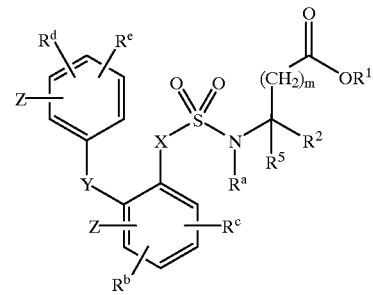

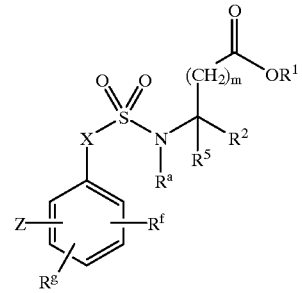

This invention also relates to a method of treatment of stroke, inflammatory diseases, septic shock reperfusion injury, Alzheimer's disease, and shigellosis, and to a pharmaceutically acceptable composition that contains a compound that is an inhibitor of interleukin-1β converting enzyme.

48 Claims, No Drawings

SULFONAMIDE SUBSTITUTED ASPARTIC ACID INTERLEUKIN-1β CONVERTING ENZYME INHIBITORS

This application claims the benefit of Provisional Application No. 60/028,323 filed Oct. 11, 1996, and a 371 of PCT/US97/18406 filed Oct. 9, 1997.

FIELD OF THE INVENTION

This invention relates to compounds that are inhibitors of interleukin-1β converting enzyme. This invention also relates to a method of treatment of stroke, inflammatory diseases, septic shock, reperfusion injury, Alzheimer's disease, shigellosis, and to a pharmaceutically acceptable composition that contains a compound that is an inhibitor of interleukin-1β converting enzyme.

BACKGROUND OF THE INVENTION

The compounds of the present invention are inhibitors of interleukin-1β converting enzyme (ICE) and are useful in treating diseases in which interleukin-1 plays a role.

ICE acts on pro-interleukin-1β (pro-IL-1β) to produce interleukin-1β (IL-1β), which is an inflammatory cytokine. In addition, ICE (Caspase-1) regulates at least four cytokines. ICE activates IL-β and IL-18, and indirectly regulates the production of IL-1 and IFNγ. Several diseases are associated with interleukin-1 activity. Examples of diseases in which interleukin-1 is involved include, but are not limited to, inflammatory diseases such as rheumatoid arthritis and inflammatory bowel disease, and neuroinflammatory disorders such as stroke. Other diseases include septic shock, reperfusion injury, Alzheimer's disease, and shigellosis.

Agents that modulate IL-1β activity have been shown to have beneficial in vivo effects. For example, compounds that are interleukin-1 receptor antagonists have been shown to inhibit ischaemic and excitotoxic damage in rat brains. See, for example, Relton J. K., et al., *Brain Research Bulletin*, 1992;29:243–246. Additionally, ICE inhibitors were shown to reduce inflammation and pyrexia in rats. See Elford P. R., et al., *British Journal of Pharmacology*, 1995;1 15:601–606.

The compounds of the present invention are also inhibitors of other cysteine proteases in the ICE family. Many of these proteases have only recently been described in the literature. While the nomenclature is still unresolved, the following proteases are representative members of this class of enzymes; Ich-2 (also called Tx or ICErel-II), ICErel-III, Ich-I (also called Nedd-2), CPP-32 (also called apopain and yama), Mch-2, Mch-3 (also called ICE-lap3, CMH-1), and Ced-3. See Henkart P. A., *Immunity*, 1996;4:195–201. It is recognized that members of this enzyme family play key biological roles in both inflammation and apoptosis (programmed cell death). In particular, Caspase-4 can activate IL-1β and IL-18. It has been shown that a murine homolog of Caspase-4 can activate ICE. Thus, inhibition of Caspase-4 will act to inhibit ICE. See Thornberry N. A., et al., *Perspectives in Drug Discovery and Design*, 1994;2:389–399.

In addition to its effects on IL-1β production, ICE has been shown to play a role in the production of the inflammatory mediator interferon-γ (Ghayur, et al., *Nature*, 1997;386(6625):619–623). ICE processes the inactive pro-form of interferon-γ inducing factor (IGIF; Interleukin-18) to active IGIF, a protein which induces production of interferon-γ by T-cells and natural killer cells. Interferon-γ has been implicated in the pathogenesis of diseases such as inflammatory disorders and septic shock. Therefore, ICE inhibitors would be expected to have beneficial effects in such disease states by effects on interferon-γ.

Recently, the nomenclature of these cysteine proteases in the ICE family (also known as Caspases with ICE being known as Caspase-1) has been further defined. The following proteases are representative members of this class of enzymes using the nomenclature described in Alnemri, et al., *Cell*, 1996;87:171: Caspase-2 (also known as Ich-1); Caspase-3 (also known as CPP32, Yama, and apopain); Caspase4 (also known as TX, Ich-2, and ICE rel-II); Caspase-5 (also known as ICE rel-III); Caspase-6 (also known as Mch2); Caspase-7 (also known as Mch3); Caspase-8 (also known as FLICE and Mch5); Caspase-9 (also known as ICE-LAP6 and Mch6); Caspase-10 (also known as Mch4).

SUMMARY OF THE INVENTION

Provided by the present invention are compounds having the Formula I

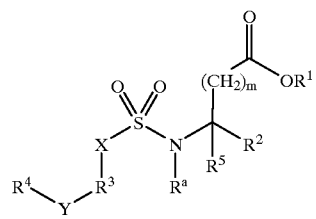

wherein
$R^1$ is hydrogen, $C_1$–$C_6$alkyl, or benzyl;
$R^2$ is —CHO, —COR$^a$, or —CN;
each $R^a$ is independently hydrogen or $C_1$–$C_6$alkyl;
X is a bond, $CH_2$, $CHR^5$, NH, $NR^5$, or O;
$R^3$ is aryl, substituted-aryl, heteroaryl, substituted-heteroaryl, cycloalkyl, substituted-cycloalkyl, heterocycle, or substituted-heterocycle;
Y is absent, $NR^5$, CO, S, O, $SO_2$, —O(CHR$^5$)$_n$—, CHR5, $NR^5$CO,

CONR$^5$,
OCHR$^5$, CHR$^5$O, SCHR$^5$, CHR$^5$S, $SO_2NR^5$, $C_1$–$C_6$alkyl,
$NR^5SO_2$, $CH_2CHR^5$, $CHR^5CH_2$, $COCH_2$, or $CH_2CO$;
$R^4$ is absent, aryl, substituted-aryl, $C_1$–$C_8$alkyl, heteroaryl, substituted-heteroaryl, cycloalkyl, $C_1$–$C_6$alkyl, substituted-cycloalkyl, heterocycloalkyl, or substituted-heterocycloalkyl;
each $R^5$ is independently hydrogen, $C_1$–$C_6$alkyl, aryl, —(CH$_2$)$_n$aryl, or —(CH$_2$)$_n$cycloalkyl;
each n is independently 0 to 5, m is 1 or 2, and the pharmaceutically acceptable salts, esters, amides, and prodrugs thereof.

In one embodiment of the invention, $R^2$ is CHO.
In another embodiment of the invention, $R^1$ is hydrogen.
In another embodiment of the invention, $R^a$ is hydrogen.
In another embodiment of the invention, X is a bond.
In another embodiment of the invention, $R^3$ is phenyl or substituted phenyl.
In another embodiment of the invention, Y is a bond.
In another embodiment of the invention, Y is O.

In another embodiment of the invention, Y is $CH_2$.

In another embodiment of the invention, $R^4$ is phenyl or substituted phenyl.

In another embodiment of the invention, $R^2$ is CHO, $R^a$ is H, $R^1$ is hydrogen, X is a bond, $R^3$ and $R^4$ are phenyl or substituted phenyl, and Y is a bond, $CH_2$, or O.

In another embodiment of the invention, m is 1 and $R^5$ is hydrogen. In a preferred embodiment, the present invention provides compounds of Formula II

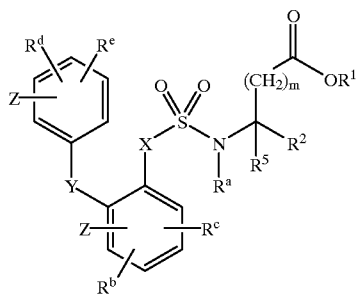

II wherein
$R^1$ is hydrogen, $C_1$–$C_6$alkyl, or benzyl;
$R^2$ is —CHO, —$COR^a$, or —CN;
each $R^a$ is independently hydrogen or $C_1$–$C_6$alkyl;
X is a bond, $CH_2$, $CHR^5$, NH, $NR^5$, or O;
Y is a bond, $NR^5$, CO, S, O, $SO_2$, $CHR^5$, $NR^5CO$, $CONR^5$, $OCHR^5$, $CHR^5O$, —$O(CHR^5)_n$—, $SCHR^5$, $CHR^5S$, $SO_2NR^5$, $NR^5SO_2$, $CH_2CHR^5$, $CHR^5CH_2$, $COCH_2$, or $CH_2CO$;
each $R^5$ is independently hydrogen, $C_1$–$C_6$alkyl, aryl, or —$(CH_2)_n$aryl;
each n is independently 0 to 5;
m is 1 or 2;
Each Z is independently hydrogen, or an aryl, substituted aryl, heteroaryl, substituted heteroaryl, cycloalkyl, substituted cycloalkyl, heterocycle, or substituted heterocycle group that is fused to the phenyl group that contains Z as a substituent;
$R^b$, $R^c$, $R^d$ and $R^e$ are each independently hydrogen, $C_1$–$C_6$alkyl, $C_1$–$C_6$alkoxy, —OH, $C_1$–$C_6$ thioalkoxy, halogen, trifluoromethyl, dialkylamino, —$NO_2$, —CN, —$CF_3$, —$CO_2$alkyl, —$SO_3H$, —CHO, —COalkyl, —CONH-alkyl, —$CONHR^q$, —CON(alkyl)$_2$, —$(CH_2)_n$—$NH_2$, —$(CH_2)_n$—NH—alkyl, —$NHR^q$, —$NHCOR^q$, —$(CH_2)_n$OH, —$(CH_2)_n$$CONH_2$, or —$(CH_2)_n$$CO_2H$; and
$R^q$ is hydrogen or $C_1$–$C_6$alkyl, and the pharmaceutically acceptable salts, esters, amides, and prodrugs thereof.

In another embodiment of the invention with respect to the compounds of Formula II, $R^1$ is hydrogen.

In another embodiment of the invention with respect to the compounds of Formula II, $R^2$ is CHO.

In another embodiment of the invention with respect to the compounds of Formula II, $R^a$ is hydrogen.

In another embodiment of the invention with respect to the compounds of Formula II, X is a bond.

In another embodiment of the invention with respect to the compounds of Formula II, Y is a bond, O, or $CH_2$.

In another embodiment of the invention with respect to the compounds of Formula II, $R^b$ and $R^c$ are hydrogen.

In another embodiment of the invention with respect to the compounds of Formula II, wherein $R^b$, $R^c$, and $R^d$ are hydrogen and $R^e$ is $C_1$–$C_6$alkyl.

In another preferred embodiment of the invention with respect to the compounds of Formula II, $R^b$ or $R^c$ is located at the para position of the phenyl ring with respect to X and $R^b$ or $R^c$ is —$OCH_3$.

In another embodiment of the invention with respect to the compounds of Formula II, m is 1 and $R^5$ is hydrogen.

In a more preferred embodiment, the present invention provides the compounds
3-(Biphenyl-2-sulfoamino)-4-oxo-butyric acid;
3-(2-Benzyl-benzenesulfonylamino)-4-oxo-butyric acid;
4-Oxo-3-(2-phenoxy-benzenesulfonylamino)-butyric acid;
4-Oxo-3-(2-p-tolyloxy-benzenesulfonylamino)-butyric acid;
3-[2-(4-Isopropyl-phenoxy)-benzenesulfonylamino]-4-oxo-butyric acid;
4-Oxo-3-(2-m-tolyloxy-benzenesulfonylamino)-butyric acid;
3-[2-(3-Isopropyl-phenoxy)-benzenesulfonylamino]-4-oxo-butyric acid; and
3-(4'-Methyl-biphenyl-2-sulfonylamino)-4-oxo-butyric acid.

This invention also includes compounds of the Formula III

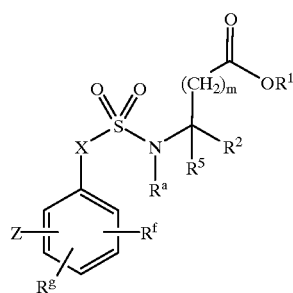

III wherein
$R^1$ is hydrogen, $C_1$–$C_6$alkyl, or benzyl;
$R^2$ is —CHO, —$COR^a$, or —CN;
each $R^a$ is independently hydrogen or $C_1$–$C_6$alkyl;
X is a bond, $CH_2$, $CHR^5$, NH, $NR^5$, or O;
$R^5$ is hydrogen, $C_1$–$C_6$alkyl, aryl, or —$(CH_2)_n$aryl;
each n is independently 0 to 5;
m is 1 or 2;
Z is absent, or an aryl, substituted aryl, heteroaryl, substituted heteroaryl, cycloalkyl, substituted cycloalkyl, heterocycle, or substituted heterocycle group that is fused to the phenyl group that contains Z as a substituent;
$R^f$, $R^g$, are each independently hydrogen, $C_1$–$C_6$alkyl, hydroxy, halogen, trifluoromethyl, dialkylamino, —$NO_2$, —CN, —$CO_2H$, —$CO_2$alkyl, —$SO_3H$, —CHO, —COalkyl, —$CONH_2$, —$CONH(CH_2)_n$aryl, —CONH $(CH_2)_n$— substituted-aryl, —CONH-alkyl, —$CONHR^q$, —CON(alkyl)$_2$, —$(CH_2)_n$—$NH_2$, —$(CH_2)_n$—NH-alkyl, —$NHR^q$, —$NHCOR^q$, —$OR^q$, —$SR^q$, or —$(CH_2)_n$aryl; and
$R^q$ is hydrogen or $C_1$–$C_8$alkyl, and the pharmaceutically acceptable salts, esters, amides, and prodrugs thereof.

In a preferred embodiment of the compounds of Formula III, $R^f$ is ortho to X on the phenyl ring, and $R^g$ is hydrogen.

In a preferred embodiment of the compounds of Formula III, Z is hydrogen, m is 1, $R^5$ is hydrogen, and $R^a$ is hydrogen.

In a preferred embodiment of the compounds of Formula III, the present invention provides the compound 3-benzenesulfonylamino-4-oxo-butyric acid.

Also provided is a method of inhibiting interleukin-1β converting enzyme, the method comprising administering to a patient in need of inhibition of interleukin-1β converting enzyme a therapeutically effective amount of a compound of Formula I, II, or III.

Also provided is a method of inhibiting Caspase-4, the method comprising administering to a patient in need of inhibition of Caspase-4 a Caspase-4 inhibiting amount of a compound of Formula I, II, or III.

Also provided is a method of treating stroke, the method comprising administering to a patient having a stroke or having had a stroke a therapeutically effective amount of a compound of Formula I, II, or III.

Also provided is a method of treating inflammatory diseases, the method comprising administering to a patient having an inflammatory disease a therapeutically effective amount of a compound of Formula I, II, or III.

Also provided is a method of treating septic shock, the method comprising administering to a patient having septic shock a therapeutically effective amount of a compound of Formula I, II, or III.

In a preferred embodiment, the inflammatory disease is arthritis or inflammatory bowel disease.

Also provided is a method of treating reperfusion injury, the method comprising administering to a patient having reperfusion injury a therapeutically effective amount of a compound of Formula I, II, or III.

Also provided is a method of treating Alzheimer's disease, the method comprising administering to a patient having Alzheimer's disease a therapeutically effective amount of a compound of Formula I, II, or III.

Also provided is a method of treating shigellosis, the method comprising administering to a patient having shigellosis a therapeutically effective amount of a compound of Formulas I, II, or III.

Also provided is a pharmaceutically acceptable composition that contains a compound of Formula I, II, or III.

DETAILED DESCRIPTION OF THE INVENTION

The present invention provides compounds having the Formula I

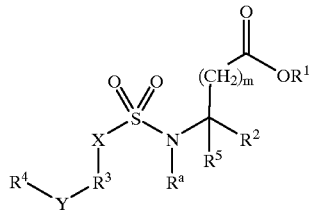

wherein
$R^1$ is hydrogen, $C_1$-$C_6$alkyl, or benzyl; $R^2$ is —CHO, —COR$^a$, or —CN;
each $R^a$ is independently hydrogen or $C_1$-$C_6$alkyl;
X is a bond, $CH_2$, $CHR^5$, NH, $NR^5$, or O;
$R^3$ is aryl, substituted-aryl, heteroaryl, substituted-heteroaryl, cycloalkyl, substituted-cycloalkyl, heterocycle, or substituted heterocycle;

Y is absent, $NR^5$, CO, S, O, $SO_2$, —O(CHR5, $NR^5$CO,

$CONR^5$,
OCHR$^5$, CHR$^5$O, SCHR$^5$, CHR$^5$S, $SO_2NR^5$, $C_1$-$C_6$alkyl, $NR^5SO_2$, $CH_2CHR^5$, $CHR^5CH_2$, $COCH_2$, or $CH_2CO$;
$R^4$ is absent, aryl, substituted-aryl, $C_1$-$C_8$alkyl, heteroaryl, substituted-heteroaryl, cycloalkyl, $C_1$-$C_6$alkyl, substituted-cycloalkyl, heterocycloalkyl, or substituted heterocycloalkyl;
each $R^5$ is independently hydrogen, $C_1$-$C_6$alkyl, aryl, —(CH$_2$)$_n$aryl, or —(CH$_2$)$_n$cycloalkyl;
each n is independently 0 to 5, m is 1 or 2, and the pharmaceutically acceptable salts, esters, amides, and prodrugs thereof.

In a preferred embodiment, the present invention provides compounds of Formula II

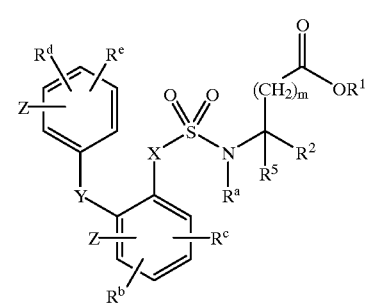

wherein
$R^1$ is hydrogen, $C_1$-$C_6$alkyl, or benzyl;
$R^2$ is —CHO, —COR$^a$, or —CN;
each $R^a$ is independently hydrogen or $C_1$-$C_6$alkyl;
X is a bond, $CH_2$, $CHR^5$, NH, $NR^5$, or O;
Y is a bond, $NR^5$, CO, S, O, $SO_2$, $CHR^5$, $NR^5CO$, $CONR^5$, $OCHR^5$, $CHR^5O$, —O(CHR$^5$)$_n$—, SCHR5, $CHR^5S$, $SO_2NR^5$, $NR^5SO_2$, $CH_2CHR^5$, $CHR^5CH_2$, $COCH_2$, or $CH_2CO$;
each $R^5$ is independently hydrogen, $C_1$-$C_6$alkyl, aryl, or —(CH$_2$)$_n$aryl;
each n is independently 0 to 5;
m is 1 or 2;
Each Z is independently hydrogen, or an aryl, substituted aryl, heteroaryl, substituted heteroaryl, cycloalkyl, substituted cycloalkyl, heterocycle or substituted heterocycle group that is fused to the phenyl group that contains Z as a substituent;
$R^b$, $R^c$, $R^d$, and $R^e$ are each independently hydrogen, $C_1$-$C_6$alkyl, $C_1$-$C_6$alkoxy, —OH, $C_1$-$C_6$thioalkoxy, halogen, trifluoromethyl, dialkylamino, —NO$_2$, —CN, —CF$_3$, —CO$_2$alkyl, —SO$_3$H, —CHO, —COalkyl, —CONH-alkyl, —CONHR$^q$, —CON(alkyl)$_2$, —(CH$_2$)$_n$—NH$_2$, —(CH$_2$)$_n$—NH-alkyl, —NHR$^q$, —NHCOR$^q$, —(CH$_2$)$_n$OH, —(CH$_2$)$_n$CONH$_2$, or —(CH$_2$)$_n$CO$_2$H; and
$R^q$ is hydrogen or $C_1$-$C_6$alkyl, and the pharmaceutically acceptable salts, esters, amides, and prodrugs thereof.

The present invention also provides compounds of the Formula III

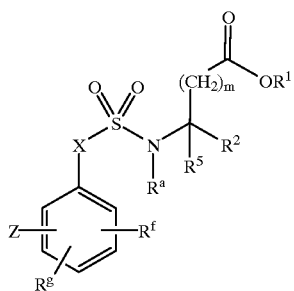

III wherein
R$^1$ is hydrogen, C$_1$–C$_6$alkyl, or benzyl;
R$^2$ is —CHO, —COR$^a$, or —CN;
each R$^a$ is independently hydrogen or C$_1$–C$_6$alkyl;
X is a bond, CH$_2$, CHR$^5$, NH, NR$^5$, or O;
R$^5$ is hydrogen, C$_1$–C$_6$alkyl, aryl, or —(CH$_2$)$_n$aryl;
each n is independently 0 to 5;
m is 1 or 2;
Z is absent, or an aryl, substituted aryl, heteroaryl, substituted heteroaryl, cycloalkyl, substituted cycloalkyl, heterocycle, or substituted heterocycle group that is fused to the phenyl group that contains Z as a substituent;
R$^f$, R$^g$, are each independently hydrogen, C$_1$–C$_6$alkyl, hydroxy, halogen, trifluoromethyl, dialkylamino, —NO$_2$, —CN, —CO$_2$H, —CO$_2$alkyl, —SO$_3$H, —CHO, —COalkyl, —CONH$_2$, —CONH(CH$_2$)$_n$aryl, —CONH (CH$_2$)$_n$— substituted-aryl, —CONH-alkyl, —CONHR$^q$, —CON(alkyl)$_2$, —(CH$_2$)$_n$—NH$_2$, —(CH$_2$)$_n$—NH-alkyl, —NHR$^q$, —NHCOR$^q$, —OR$^q$, —SR$^q$, or —(CH$_2$)$_n$aryl; and
R$^1$ is hydrogen or C$_1$–C$_8$alkyl, and the pharmaceutically acceptable salts, esters, amides, and prodrugs thereof.

In general, the groups X and Y in Formulas I, II, and III are spacers for the groups attached to X and Y. It is also noted that certain compounds of Formulas I, II, and III can exist in different, interconvertible forms. An example is shown below when R$^1$ is hydrogen and R$^2$ is CHO.

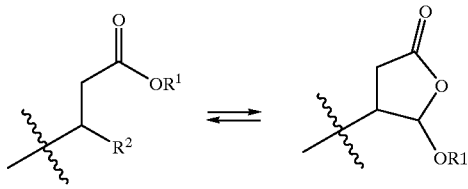

Both the cyclic and acyclic forms are contemplated and are considered part of the present invention. Moreover, it is preferred that the groups attached to R$^3$ be attached at adjacent atoms of R$^3$. For example, if R$^3$ is phenyl, X and Y would have a 1, 2 relationship on R$^3$.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "alkoxy" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The term "aryl" means an aromatic hydrocarbon. Representative examples of aryl groups include phenyl and naphthyl.

The term "heteroatom" includes oxygen, nitrogen, sulfur, and phosphorus.

The term "heteroaryl" means an aryl group wherein one or more carbon atom of the aromatic hydrocarbon has been replaced with a heteroatom. Examples of heteroaryl groups include furan, thiophene, pyrrole, thiazole, pyridine, pyrimidine, pyrazine, benzofuran, indole, coumarin, quinoline, isoquinoline, and naphthyridine.

The term "cycloalkyl" means a cyclic alkyl group. Examples of cycloalkyl groups include cyclopropane, cyclobutane, cyclopentane, and cyclohexane.

The term "heterocycle" means a cycloalkyl group on which one or more carbon atom has been replaced with a heteroatom. Examples of heterocycles include piperazine, morpholine, and piperidine.

The aryl, heteroaryl, or cycloalkyl groups may be substituted with one or more substituents, which can be the same or different. Examples of suitable substituents include alkyl, alkoxy, thioalkoxy, hydroxy, halogen, trifluoromethyl, amino, alkylamino, dialkylamino, —NO$_2$, —CN, —CO$_2$H, —CO$_2$alkyl, —SO$_3$H, —CHO, —COalkyl, —CONH$_2$, —CONH-alkyl, —CONHR$^q$, —CON(alkyl)$_2$, —(CH$_2$)$_n$—NH$_2$, —OH, —CF$_3$, —OC$_1$–C$_6$alkyl, —(CH$_2$)$_n$—NH-alkyl, —NHR$_q$, —NHCOR$^q$, phenyl,

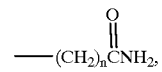

where n is 1 to 5 and R$^q$ is hydrogen or alkyl.
The symbol "—" means a bond.
The compounds of Formula I, II, and III can be administered to a patient either alone or as part of a pharmaceutically acceptable composition. The compositions can be administered to patients such as humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents or vehicles, include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar, as well as, high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofuryl alcohol, polyethyleneglycols, and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures, but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 1,000 mg per day. For a normal human adult having a body weight of about 70 kg, a dosage in the range of about 0.01 to about 100 mg per kilogram of body weight per day is preferable. The specific dosage used, however, can vary. For example, the dosage can depend on a numbers of factors including the requirements of the patient, the severity of the condition being treated, and the pharmacological activity of the compound being used. The determination of optimum dosages for a particular patient is well known to those skilled in the art.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic and tautomeric forms, where possible, of the compounds of the invention. The term "salts" refers to the relatively nontoxic, inorganic, and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laureate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as nontoxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Berge S. M, et al., "Pharmaceutical Salts", *J. Pharm. Sci.,* 1977;66:1–19 which is incorporated herein by reference).

Examples of pharmaceutically acceptable, nontoxic esters of the compounds of this invention include $C_1$–$C_6$alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$alkyl esters are preferred. Esters of the compounds of the present invention may be prepared according to conventional methods.

Examples of pharmaceutically acceptable, nontoxic amides of the compounds of this invention include amides derived from ammonia, primary $C_1$–$C_6$alkyl amines and secondary $C_1$–$C_6$dialkyl amines wherein the alkyl groups are straight or branched chain. In the case of secondary amines the amine may also be in the form of a 5- or 6-membered heterocycle containing one nitrogen atom.

Amides derived from ammonia, $C_1$–$C_3$alkyl primary amines, and $C_1$–$C_2$dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can exist in different stereoisomeric forms by virtue of the presence of asymmetric centers in the compounds; i.e., each asymmetric carbon can have either the R or S configuration. It is contemplated that all stereoisomeric forms of the compounds as well as mixtures thereof, including racemic mixtures, form part of this invention.

The compounds of the present invention are administered to a patient in need of ICE inhibition. In general, patients in need of ICE inhibition are those patients having a disease or condition in which ICE plays a role. Examples of such diseases include, but are not limited to, inflammatory diseases such as rheumatoid arthritis and inflammatory bowel disease and neuroinflammatory disorders such as stroke. Other diseases include reperfusion injury, Alzheimer's disease, and shigellosis.

A "therapeutically effective amount" is an amount of a compound of Formula I, II, or III that when administered to a patient having a disease that can be treated with a compound of Formula I ameliorates a symptom of the disease. A therapeutically effective amount of a compound of Formula I, II, or III is readily determined by one skilled in the art by administering a compound of Formula I, II, or III to a patient and observing the results.

The following examples illustrate particular embodiments of the invention and are not intended to limit the scope of the specification and claims in any manner.

The compounds of the present invention can be made generally as follows.

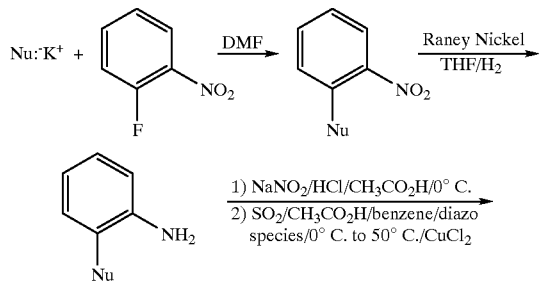

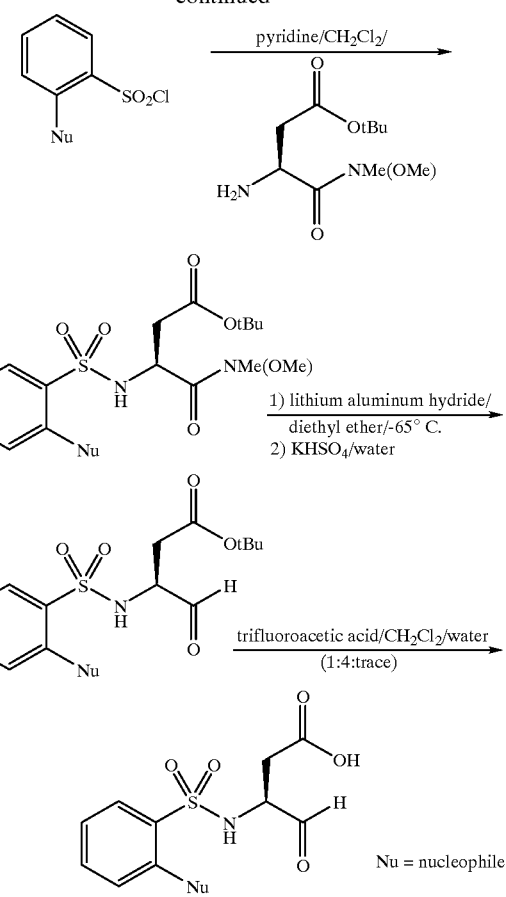

EXAMPLE 1

3-(Biphenyl-2-Sulfoamino)-4-Oxo-Butyric Acid

Biphenyl-2-sulfonyl chloride was obtained using a known procedure (Neale A. J., Rawlings T. J., McCall E. B., *Tetrahedron*, 1965;21:1299–1313). In general, the sulfonyl chloride (3.2 mmol) was stirred in dichloromethane (20 mL) with pyridine (12 mmol) and Asp(OtBu)—NMe(OMe) [Asp=aspartic acid; tBu=tert-butyl; Me=methyl] (2.9 mmol). After stirring 16 hours at room temperature, dichloromethane was added, and the organic layer was washed sequentially with 10% sulfuric acid, water, and then brine. Removal of the solvent provided the product as a colorless foam. Chromatography on silica gel eluting with 7:3 diethyl ether/hexanes gave product as a colorless foam (750 mg, 56%). The resulting sulfonamide was dissolved diethyl ether and cooled to −65° C. Lithium aluminum hydride (1.5 equivalents) was added to the solution and the reaction temperature was maintained for 2 hours. The excess hydride was quenched by the addition of potassium hydrogen sulfate (2 equivalents) dissolved in water. After warming to room temperature, ether was added and the organic layer was washed with water and then brine. The solvent was evaporated to give crude product as a colorless oil. Chromatography on silica gel (3:2 ether/hexanes) gave the aldehyde (327 mg, 50%). The aldehyde was treated with 3:1 dichloromethane/trifluoroacetic acid (20 mL) containing a trace of water for 2 hours. The solvent was evaporated, excess trifluoroacetic acid was chased with toluene and then ether to give product as a colorless foam (242 mg, 90%).

¹H NMR (CD₃OD) as the lactol 8.05 (m, 1H), 7.60 (t, 1H), 7.53 (t, 1H), 7.41 (m, 5H), 7.30 (d, 1H), 4.42 (s, 1H), 3.63 (s, 1H), 2.50 (m, 1H), 2.30 (m, 1H);
Mass Spectrometry—Chemical Ionization (MS CI)+1% NH₃ in CH₄ 334 (M+H)⁺.

EXAMPLE 2

3-Benzenesulfonylamino-4-Oxo-Butyric Acid

Benzenesulfonyl chloride was employed to acylate the amine of Asp(OtBu)—NMe(OMe); from the resulting sulfonamide, final product was obtained as a colorless foam employing the methods previously described in Example 1. ¹H NMR (CD₃OD) as the lactol 7.87 (m, 2H), 7.58 (m, 3H), 4.44, 4.38 (d, 1H), 3.74 (m, 1H), 2.57 (m, 1H), 2.27 (m, 1H); MS CI+1% NH₃ in CH₄ 240 (M—OH)⁺.

EXAMPLE 3

3-(2-Benzyl-Benzenesulfonylamino)-4-Oxo-Butyric Acid

Diphenylmethane-2-sulfonyl chloride was employed to acylate the amine of Asp(OtBu)—NMe(OMe); from the resulting sulfonamide, final product was obtained as a colorless foam (62 mg, 9%) employing the methods previously described in Example 1. ¹H NMR (CD₃OD) as the lactol 8.00 (dd, 1H), 7.42 (t, 1H), 7.25 (m, 6H), 7.05 (dd, 1H), 4.54, 4.50 (d, 1H), 4.01 (s, 2H), 3.63 (m, 1H), 2.58 (m, 1H), 2.37 (m, 1H);
MS Cl+1% NH₃ in CH₄ 304 (M—CHO)⁺.

EXAMPLE 4

4-Oxo-3-(2-Phenoxy-Benzenesulfonylamino)-Butyric Acid

Diphenylether-2-sulfonyl chloride was employed to acylate the amine of Asp(OtBu)—NMe(OMe); from the resulting sulfonamide, final product was obtained as a colorless foam (72 mg, 7%) employing the methods previously described in Example 1. ¹H NMR (CD₃OD) as the lactol 7.95 (d, 1H), 7.43 (m, 3H), 7.20 (m, 4H), 6.82 (d, 1H), 4.58, 4.52 (d, 1H), 3.75 (m, 1H), 2.70–2.40 (m, 2H);
MS APCI probe temperature 450° C., cone voltage 25 volts, acetonitrile: methanol 4:1, 350.5 (M+H)⁺.

EXAMPLE 5

4-Oxo-3-(2-p-Tolyloxy-Benzenesulfonylamino)-Butyric Acid (4'-Methylphenyl) phenylether-2-sulfonyl chloride was employed to acylate the amine of Asp(OtBu)—NMe(OMe); from the resulting sulfonamide, final product was obtained as a colorless foam (152 mg, 15%) employing the methods previously described in Example 1. ¹H NMR (CD₃OD) as the lactol 7.90 (d, 1H), 7.48 (d, 1H), 7.35–7.00 (m, 5H), 6.80 (d, 1H), 4.55, 4.50 (d, 1H), 3.75 (m, 1H), 2.70–2.42 (m, 2H), 2.35 (s, 3H);
MS APCI probe temperature. 450° C., cone voltage 25 volts, acetonitrile: methanol 4:1, 363.1 (M+H)⁺.

EXAMPLE 6

3-[2-(4-Isopropyl-Phenoxy)-Benzenesulfonylamino]-4-Oxo-Butyric Acid (4'-Isopropylphenyl)phenylether-2-sulfonyl chloride was employed to acylate the amine of Asp(OtBu)—NMe(OMe); from the resulting sulfonamide, final product was obtained as a colorless foam (248 mg, 22%) employing the methods previously described in Example 1. ¹H NMR (CD₃OD) as the lactol 7.92 (d, 1H), 7.50 (t, 1H), 7.32 (m, 2H), 7.13 (m, 3H), 6.82 (d, 1H), 4.58, 4.52 (d, 1H), 3.75 (m, 1H), 2.95 (m, 1H), 2.70–2.42 (m, 2H), 1.25 (d, 6H);
MS APCI probe temperature 450° C., cone voltage 25 volts, acetonitrile: methanol 4:1, 392.4 (M+H)⁺.

EXAMPLE 7

4-Oxo-3-(2-m-Tolyloxy-Benzenesulfonylamino)-Butyric Acid (3'-Methylphenyl) phenylether-2-sulfonyl chloride was employed to acylate the amine of Asp(OtBu)—NMe(OMe); from the resulting sulfonamide, final product was obtained as a colorless foam (85 mg, 8%) employing the methods previously described in Example 1. ¹H NMR (CD₃OD) as the lactol 7.90 (d, 1H), 7.50 (t, 1H), 7.35–7.13 (m, 2H), 7.10–6.80 (m, 4H), 4.58–4.52 (d, 1H), 3.76 (m, 1H), 2.65–2.42 (m, 2H), 2.35 (s, 3H);
MS APCI probe temperature 450° C., cone voltage 25 volts, acetonitrile: methanol 4:1, 363.1 (M+H)⁺.

EXAMPLE 8

3-[2-(3-lsopropyl-Phenoxy)-Benzenesulfonylamino]-4-Oxo-Butyric Acid (3'-Isopropylphenyl) phenylether-2-sulfonyl chloride was employed to acylate the amine of Asp(OtBu)—NMe(OMe); from the resulting sulfonamide, final product was obtained as a colorless foam (334 mg, 29%) employing the methods previously described in Example 1. ¹H NMR (CD₃OD) as the lactol 7.90 (d, 1H), 7.50 (t, 1H), 7.45 (m, 1H), 7.25–6.80 (m, 5H), 4.58, 4.52 (d, 1H), 3.78 (m, 1H), 2.90 (m, 1H), 2.70–2.40 (m, 2H), 1.25 (d, 6H);
MS APCI probe temperature 450° C., cone voltage 25 volts, acetonitrile: methanol 4:1, 392.5 (M+H)⁺.

EXAMPLE 9

3-(4'-Methyl-Biphenyl-2-Sulfonylamino)-4-Oxo-Butyric Acid (4'-Methyl)biphenyl-2-sulfonyl chloride was employed to acylate the amine of Asp(OtBu)—NMe(OMe); from the resulting sulfonamide, final product was obtained as a colorless foam (334 mg, 29%) employing the methods previously described.
¹H NMR (CD₃OD) as the lactol 8.03 (m, 1H), 7.60 (m, 1H), 7.50 (m, 1H), 7.35 (m, 3H), 7.21 (m, 2H), 4.41 (d, 1H), 4.60 (m, 1H), 2.45 (m, 1H), 2.40 (s, 3H), 2.35 (m, 1H);
MS APCI probe temperature 450° C., cone voltage 25 volts, acetonitrile: methanol 4:1, 348.5 (M+H)⁺.

EXAMPLE 10

3-(2-Isobutoxy-Benzenesulfonylamino)-4-Oxo-Butyric Acid 2-(Isobutoxy)-benzenesulfonyl chloride was employed to acylate the amine of Asp(OtBu)—NMe(OMe). From the resulting sulfonamide, final product was obtained as a colorless foam (112 mg, 56%) employing methods previously described. ¹H NMR (CD₃OD) as the lactol 7.81 (m, 1H), 7.58 (m, 1H), 7.17 (dd, 1H), 7.05 (m, 1H), 4.50, 4.40 (d, 1H), 3.85 (d, 2H), 3.61 (m, 1H), 2.45 (m, 2H), 2.20 (m, 1H), 1.04 (d, 6H); MS APCI Probe temperature 450° C., cone voltage 25 volts, acetonitrile, 330.5 (M+H)⁺.

EXAMPLE 11

3-[2-(2-Methyl-Pentanoylamino)-Benzenesulfonylamino]-4-Oxo-Butyric Acid

2-Nitrobenzenesulfonyl chloride was employed to acylate the amine of Asp(OtBu)—NMe(OMe) employing methods previously described. The resulting nitrosulfonamide was reduced employing 5% Pd on carbon and hydrogen gas to provide the aminosulfonamide $^1$H NMR (CDCl$_3$) 7.70 (d, 1H), 7.30 (t, 1H), 6.76 (m, 2H), 5.92 (d, 1H), 4.60 (m, 1H), 3.63 (s, 3H), 3.02 (s, 3H), 2.62–2.39 (m, 2H), 1.42 (s, 9H); MS CI+1% NH$_3$ in CH$_4$332 (M—tBu)$^+$. The aminosulfonamide (400 mg, 1.0 mmol) was acylated employing 2-methylopentanoyl chloride (1.5 mmol) and triethylamine (3 mmol) in dichloromethane (5 mL). Chromatography of the crude reaction product (4:1, diethyl ether, hexane) gave the acylated amine (148 mg, 30%) $^1$H NMR (CDCl$_3$) 9.34 (d, 1H), 8.55 (dd, 1H), 7.86 (d, 1H), 7.55 (t, 1H), 7.17 (t, 1H), 5.90 (d, 1H), 4.51 (m, 1H), 3.58 (s, 3H), 3.03 (m, 3H), 2.43 (m, 3H), 1.80–1.25 (m, 4H), 1.40 (s, 9H), 1.22 (d, 3H), 0.94 (t, 3H); MS APCI Probe temperature 450° C., cone voltage 25 volts, acetonitrile:methanol 4:1, 486.6 (M+H)$^+$. Final product was obtained from this sulfonamide employing methods previously described. 1H NMR (CD$_3$OD) as the lactol 8.30 (m, 1H), 7.93 (m, 1H), 7.64–7.20 (m, 4H), 4.50–4.25 (m, 2H), 3.63 (m, 1H), 2.73–2.20 (m, 3H), 1.65 (m, 1H), 1.42 (m, 2H), 1.22 (d, 3H), 0.97 (t, 3H).

EXAMPLE 12

4-Oxo-3-(2-o-Tolyloxy-Benzenesulfonylamino)-Butyric Acid 2-(o-Tolyloxy)-benzenesulfonyl chloride was employed to acylate the amine of Asp(OtBu)—NMe(OMe). From the resulting sulfonamide, final product was obtained as a colorless foam (206 mg, 66%) employing methods previously described. 1H NMR (CD$_3$OD) as the lactol; 7.90 (m, 1H), 7.43 (m, 1H), 7.38–7.08 (m, 5H), 6.62 (d, 1H), 4.58 (dd, 1H), 3.79 (m, 1H), 2.70–2.42 (m, 2H), 2.03 (m, 3H); MS APCI Probe temperature 450° C., cone voltage 25 volts, acetonitrile:methanol 4:1, 364.4 (M+H)$^+$.

EXAMPLE 13

4-Oxo-3-(2-Phenethyl-Benzenesulfonylamino)-Butyric Acid 2-(Phenethyl)-benzenesulfonyl chloride was employed to acylate the amine of Asp(OtBu)—NMe(OMe). From the resulting sulfonamide, final product was obtained as a colorless foam (56 mg, 25%) employing methods previously described. $^1$H NMR (CD$_3$OD) as the lactol; 8.00 (m, 1H), 7.60–7.10 (m, 8H) 4.50, 4.45 (d, 1H), 3.63 (m, 1H), 3.30 (m, 2H), 2.97 (m, 2H), 2.62–2.42 (m, 2H); MS APCI Probe temperature 450° C., cone voltage 25 volts, acetonitrile:methanol 4:1, 362.5 (M+H)$^+$.

EXAMPLE 14

3-(2-Cyclohexyloxy-Benzenesulfonylamino)-4-Oxo-Butyric Acid 2-(Cyclohexyloxy)-benzenesulfonyl chloride was employed to acylate the amine of Asp(OtBu)—NMe(OMe). From the resulting sulfonamide, final product was obtained as a colorless foam (190 mg, 95%) employing methods previously described. $^1$H NMR (CD$_3$OD) as the lactol; 7.80 (m, 1H), 7.57 (m, 1H), 7.23–6.98 (m, 2H), 4.58 (m, 1H), 4.50, 4.40 (d, 1H), 3.63 (m, 1H), 2.45 (m, 2H), 2.10–1.40 (m, 10H); MS APCI Probe temperature 450° C., cone voltage 25 volts, acetonitrile:methanol 4:1, 356.5 (M+H)$^+$.

EXAMPLE 15

3-[2-(1-Chloro-Naphthalen-2-Yloxy)-Benzenesulfonylamino]-4-Oxo-Butyric Acid 2-(1-Chloro-naphthalen-2-yloxy)-benzenesulfonyl chloride was employed to acylate the amine of Asp(OtBu)—NMe(OMe). From the resulting sulfonamide, final product was obtained as a colorless foam (199 mg, 92%) employing methods previously described. $^1$H NMR (CD$_3$OD) as the lactol; 8.30 (d, 1H), 7.93 (m, 3H), 7.70 (m, 1H), 7.60 (m, 1H), 7.48 (m, 1H), 7.39 (m, 1H), 7.20 (m, 1H), 6.75 (d, 1H), 4.63, 4.58 (d, 1H), 3.83 (m, 1H), 2.40 (m, 2H); MS APCI Probe temperature 450° C., cone voltage 25 volts, acetonitrile:methanol 4:1, 434.4 (M+H)$^+$.

EXAMPLE 16

4-Oxo-3-[2-(5,6,7,8-Tetrahydro-Naphthalen-2-Yloxy)-Benzenesulfonylamino]-Butyric Acid 2-(5,6,7,8-tetrahydro-naphthalen-2-yloxy)-benzenesulfonyl chloride was employed to acylate the amine of Asp(OtBu)—NMe(OMe). From the resulting sulfonamide, final product was obtained as a colorless foam (205 mg, 87%) employing methods previously described. $^1$H NMR (CD$_3$OD) as the lactol; 7.90 (m, 1H), 7.42 (m, 1H), 7.17 (m, 2H), 7.00 (d, 2H), 6.90 (m, 1H), 6.62 (d, 2H), 4.58,4.46 (d, 1H), 3.78 (m, 1H), 2.81 (m, 2H), 2.63 (m, 2H), 2.50 (m, 2H), 1.80 (m, 4H); MS APCI Probe temperature 450° C., cone voltage 25 volts, acetonitrile:methanol 4:1, 404.5 (M+H)$^+$.

EXAMPLE 17

4-Oxo-3-(2-Phenethyloxy-Benzenesulfonylamino)-Butyric Acid 2-phenethyloxy-benzenesulfonyl chloride was employed to acylate the amine of Asp(OtBu)—NMe(OMe). From the resulting sulfonamide, final product was obtained as a colorless foam (224 mg, 69%) employing methods previously described. 1H NMR (CD$_3$OD) as the lactol; 7.78 (m, 1H), 7.55 (m, 1H), 7.42–7.00 (m, 7H), 4.35 (m, 2H), 4.30, 4.20 (d, 1H), 3.55 (m, 1H), 3.20 (t, 2H), 2.52–2.14 (m, 2H); MS APCI Probe temperature 450° C., cone voltage 25 volts, acetonitrile:methanol 4:1, 378.4 (M+H)$^+$.

EXAMPLE 18

3-[2-(2-Ethyl-Phenoxy)-Benzenesulfonylamino]-4-Oxo-Butyric Acid 2-(2-Ethyl-phenoxy)-benzenesulfonyl chloride was employed to acylate the amine of Asp(OtBu)—NMe(OMe). From the resulting sulfonamide, final product was obtained as a colorless foam (295 mg, 70%) employing methods previously described. $^1$H NMR (CD$_3$OD) as the lactol; 7.92 (m, 1H), 7.40 (m, 2H), 7.30–7.05 (m, 4H), 6.63 (d, 1H), 4.58, 4.56 (d, 1H), 3.78 (m, 1H), 2.60–2.42 (m, 4H), 1.16 (t, 1H); MS APCI Probe temperature 450° C., cone voltage 25 volts, acetonitrile:methanol 4:1, 378.4 (M+H)$^+$.

EXAMPLE 19

3-[2-(4-Sec-Butyl-Phenoxy)-Benzenesulfonylamino]-4-Oxo-Butyric Acid 2-(4-sec-Butyl-phenoxy)-benzenesulfonyl chloride was employed to acylate the amine of Asp(OtBu)—NMe(OMe).

From the resulting sulfonamide, final product was obtained as a colorless foam (295 mg, 70%) employing methods previously described. 1H NMR (CD$_3$OD) as the lactol; 7.92 (m, 1H), 7.48 (t, 1H), 7.30–7.07 (m, sH), 6.82 (d, 1H), 4.56, 4.53 (d, 1H), 3.75 (m, 1H), 2.70–2.43 (m, 3H), 1.62 (m, 2H), 1.24 (d, 3H), 0.83 (t, 3H); MS APCI Probe temperature 450° C., cone voltage 25 volts, acetonitrile:methanol 4:1, 406.5 (M+H)$^+$.

EXAMPLE 20

3-[2-(Biphenyl-4-Yloxy)-Benzenesulfonylamino]-4-Oxo-Butyric Acid 2-(Biphenyl-4-yloxy)-benzenesulfonyl chloride was employed to acylate the amine of Asp(OtBu)—NMe(OMe). From the resulting sulfonamide, final product was obtained as a colorless foam (334 mg, 88%) employing methods previously described. 1H NMR (CD$_3$OD) as the lactol; 7.95 (m, 1H), 7.63 (m, 4H), 7.58–7.08 (m, 7H0, 6.94 (d, 1H), 4.59, 4.55 (d, 1H), 3.75 (m, 1H), 2.57 (m, 2H); electrospray MS (50:50 acetonitrile:water+0.1% NH$_4$OH) m/z 424.1 (M–H)$^-$.

EXAMPLE 21

3-{2-[4-(1-Methyl-Pentyl)-Phenoxy]-Benzenesulfonylamino}-4-Oxo-Butyric Acid

2-[4-(1-Methyl-pentyl)-phenoxy]-benzenesulfonyl chloride was employed to acylate the amine of Asp(OtBu)—NMe(OMe). From the resulting sulfonamide, final product was obtained as a colorless foam (158 mg, 69%) employing methods previously described. 1H NMR (CD$_3$OD) as the lactol; 7.90 (m, 1H), 7.47 (m, 1H), 7.30–7.05 (m, 5H), 6.82 (d, 1H), 4.58, 4.52 (d, 1H), 3.75 (m, 1H), 2.80–2.43 (m, 3H), 1.58 (q, 2H), 1.12 (m, 7H), 0.83 (t, 3H); electrospray MS (50:50 acetonitrile:water+0.1% NH$_4$OH) m/z 432.1 (M–H)$^-$.

EXAMPLE 22

3-[2-(4-Isopropyl-3-Methyl-Phenoxy)-Benzenesulfonylamino]-4-Oxo-Butyric Acid 2-(4-Isopropyl-3-methyl-phenoxy)-benzenesulfonyl chloride was employed to acylate the amine of Asp(OtBu)—NMe(OMe). From the resulting sulfonamide, final product was obtained as a colorless foam (382 mg, 79%) employing methods previously described. 1H NMR (CD$_3$OD) as the lactol; 7.87 (m, 1H), 7.45 (t, 1H), 7.30 (m, 1H), 7.15 (m, 1H), 6.95 (m, 2H), 6.82 (d, 1H), 4.58, 4.52 (d, 1H), 3.75 (m, 1H), 3.17 (m, 1H), 2.57 (m, 2H), 2.33 (s, 3H), 1.23 (d, 6H); electrospray MS (50:50 acetonitrile:water+0.1% NH$_4$OH) m/z 404.0.1 (M–H)$^-$.

EXAMPLE 23

3-(2-Benzyloxy-Benzenesulfonylamino)-4-Oxo-Butyric Acid

2-Benzyloxy-benzenesulfonyl chloride was employed to acylate the amine of Asp(OtBu)—NMe(OMe). From the resulting sulfonamide, final product was obtained as a colorless foam (137 mg, 91%) employing methods previously described. $^1$H NMR (CD$_3$OD) as the lactol; 7.83 (m, 1H), 7.55 (m, 3H), 7.37 (m, 3H), 7.20 (m, 1H), 7.06 (m, 1H), 5.28 (s, 2H), 4.45, 4.41 (d, 1H), 3.64 (m, 1H) 2.60–2.30 (m, 2H), MS APCI Probe temperature 450° C., cone voltage 25 volts, acetonitrile:methanol 4:1, 362.0 (M–H)$^-$.

EXAMPLE 24

3-[2-(2, 3-Dimethyl-Phenoxy)-Benzenesulfonylamino]-4-Oxo-Butyric Acid 2-(2,3-Dimethyl-phenoxy)-benzenesulfonyl chloride was employed to acylate the amine of Asp(OtBu)—NMe(OMe). From the resulting sulfonamide, final product was obtained as a colorless foam (373 mg, 82%) employing methods previously described. $^1$H NMR (CD$_3$OD) as the lactol; 7.90 (m, 1H), 7.42 (m, 1H), 7.17 (m, 3H), 6.97 (m, 1H), 6.58 (d, 1H), 4.58, 4.55 (d, 1H), 3.79 (m, 1H), 2.68–2.44 (m, 2H), 2.33 (s, 3H), 2.14 (s, 3H)MS APCI Probe temperature 450° C., cone voltage 25 volts, acetonitrile:methanol 4:1, 375.8 (M–H)$^-$.

EXAMPLE 25

3-{2-[4-(1-Ethyl-Propyl)-Phenoxy]-Benzenesulfonylamino}-4-Oxo-Butyric Acid

2-[4-(1-Ethyl-propyl)-phenoxy]-benzenesulfonyl chloride was employed to acylate the amine of Asp(OtBu)—NMe(OMe). From the resulting sulfonamide, final product was obtained as a colorless foam (467 mg, 67%) employing methods previously described. $^1$H NMR (CD$_3$ OD) as the lactol; 7.92 (m, 1H), 7.45 (t, 1H), 7.17 (m, 5H), 6.83 (d, 1H), 4.58, 4.53 (d, 1H), 3.77 (m, 1H), 2.68–2.30 (m, 3H), 1.73 (m, 2H), 1.58 (m, 2H), 0.79 (t, 6H);MS APCI Probe temperature 450° C., cone voltage 25 volts, acetonitrile:methanol 4:1, 417.9 (M–H)$^-$.

EXAMPLE 26

4-Oxo-3-[2-(3,4,5-Trimethyl-Phenoxy)-Benzenesulfonylamino]-Butyric Acid 2-(3,4,5-trimethyl-phenoxy) -benzenesulfonyl chloride was employed to acylate the amine of Asp(OtBu)—NMe(OMe). From the resulting sulfonamide, final product was obtained as a colorless foam (407 mg, 79%) employing methods previously described. $^1$H NMR (CD$_3$OD) as the lactol; 7.88 (m, 1H), 7.44 (t, 1H), 7.16 (m, 2H), 6.80 (m, 3H), 4.58, 4.54 (d, 1H), 3.75 (m, 1H), 2.65–2.43 (m, 2H), 2.28 (s, 6H), 2.18 (s, 3H); MS APCI Probe temperature 450° C., cone voltage 25 volts, acetonitrile:methanol 4:1, 389.8 (M–H)$^-$.

EXAMPLE 27

3-(2-Sec-Butoxy-Benzenesulfonylamino)-4-Oxo-Butyric Acid 2-sec-Butoxy -benzenesulfonyl chloride was employed to acylate the amine of Asp(OtBu)—NMe(OMe). From the resulting sulfonamide, final product was obtained as a colorless foam (450 mg, 73%) employing methods previously described. 1H NMR (CD$_3$OD) as the lactol; 7.80 (m, 1H), 7.55 (m, 1H), 7.18 (m, 1H), 7.02 (m, 1H), 4.70 (m, 1H), 4.53, 4.42 (d, 1H), 3.65 (m, 1H), 2.45 (m, 2H), 1.88 (m, 1H), 1.75–1.38 (m, 3H), 1.38 (dd, 3H), 0.97 (dt, 3H); MS APCI Probe temperature 450° C., cone voltage 25 volts, acetonitrile:methanol 4:1, 342.1 (M–H)$^-$.

EXAMPLE 28

3-[2-(4-Sec-Butyl-3-Methyl-Phenoxy)-Benzenesulfonylamino]-4-Oxo-Butyric Acid 2-(4-sec-Butyl-3-methyl-phenoxy)-benzenesulfonyl chloride was employed to acylate the amine of Asp(OtBu)—

NMe(OMe). From the resulting sulfonamide, final product was obtained as a colorless foam (257 mg, 69%) employing methods previously described. 1H NMR (CD$_3$OD) as the lactol; 7.90m, 1H), 7.45 (t, 1H), 7.18 (m, 2H), 6.98 (m, 2H), 6.83 (d, 1H), 4.57, 4.53 (d, 1H), 3.75 (m, 1H), 2.94 (m, 1H), 2.58 (m, 2H), 2.32 (s, 3H), 1.63 (m, 2H), 1.21 (d, 3H), 0.86 (t, 3H); MS APCI Probe temperature 450° C., cone voltage 25 volts, acetonitrile:methanol 4:1, 420.1 (M+H)$^+$.

EXAMPLE 29

3-(2-Ethylbutoxy-Benzenesulfonylamino)-4-Oxo-Butyric Acid

2-Ethylbutoxy-benzenesulfonyl chloride was employed to acylate the amine of Asp(OtBu)—NMe(OMe). From the resulting sulfonamide, final product was obtained as a colorless foam (113 mg, 51%) employing methods previously described. 1H NMR (CD$_3$OD) as the lactol; 7.85 (m, 1H), 77.65 (m, 1H), 7.17 (m, 1H), 7.00 (m, 1H), 4.45, 4.35 (d, 1H), 4.05 (m, 2H0, 3.72 (m, 1H), 2.45 (m, 2H), 1.77 (m, 1H), 1.58 (m, 4H), 0.95 (t, 6H); MS APCI Probe temperature 450° C., cone voltage 25 volts, acetonitrile:methanol 4:1, 356.1 (M–H)$^-$.

EXAMPLE 30

3-(2-Methylbutoxy-Benzenesulfonylamino)-4-Oxo-Butyric Acid

2-Methylbutoxy-benzenesulfonyl chloride was employed to acylate the amine of Asp(OtBu)—NMe(OMe). From the resulting sulfonamide, final product was obtained as a colorless foam (450 mg, 73%) employing methods previously described. 1H NMR (CD$_3$OD) as the lactol; 7.80 (m, 1H), 7.55 (m, 1H), 7.18 (m, 1H), 7.04 (m, 1H), 4.68 (m, 1H), 4.52, 4.42 (d, 1H), 3.65 (m, 1H), 2.43 (m, 2H), 1.84 (m, 1H), 1.75–1.40 (m, 3H), 1.37 (m, 3H), MS APCI Probe temperature 450° C., cone voltage 25 volts, acetonitrile:methanol 4:1, 342.1 (M–H)$^-$.

EXAMPLE 31

4-Oxo-3-[2-(1-Naphthyl)Ethyloxy]-Benzenesulfonylamino)-Butyric Acid 2-(1-Naphthyl)ethyloxy-benzenesulfonyl chloride was employed to acylate the amine of Asp(OtBu)—NMe(OMe). From the resulting sulfonamide, final product was obtained as a pink foam (120 mg, 90%) employing methods previously described. $^1$H NMR (CD$_3$OD) as the lactol; 8.23 (d, 1H), 7.92 (d, 1H), 7.80 (m, 2H), 7.55 (m, 4H), 7.15 (m, 2H), 7.03 (m, 1H), 4.55 (m, 2H), 4.20, 4.03 (d, 1H), 3.74 (m, 2H), 3.60 (m, 1H), 2.44–2.10 (m, 2H); MS APCI Probe temperature 450° C., cone voltage 25 volts, acetonitrile:methanol 4:1, 428.1 (M+H)$^+$.

EXAMPLE 32

3-(2'-Methyl-Biphenyl-2-Sulfonylamino)-4-Oxo-Butyric Acid

2'-Methyl-biphenyl-sulfonyl chloride was employed to acylate the amine of Asp(OtBu)—NMe(OMe). From the resulting sulfonamide, final product was obtained as a colorless foam (70 mg, 84%) employing methods previously described. $^1$H NMR (CD$_3$OD) as the lactol 8.08 (m, 1H), 7.61 (m, 1H), 7.58 (m, 1H), 7.10–7.25 (m, 5H), 4.52, 4.41 (d, 1H), 3.70 (m, 1H), 2.45 (m, 2H), 2.03 (s, 3H); MS APCI Probe temperature 450° C., cone voltage 25 volts, acetonitrile, 348.4 (M+H)$^+$.

EXAMPLE 33

3-(2-Naphthalen-1-yl-Benzenesulfonylamino)-4-Oxo-Butyric Acid

2-Naphthalen-1-yl-benzenesulfonyl chloride was employed to acylate the amine of Asp(OtBu)—NMe(OMe). From the resulting sulfonamide, final product was obtained as a colorless foam (110 mg, 71%) employing methods previously described. $^1$H NMR (CD$_3$OD) as the lactol; 8.18 (m, 1H), 7.90 (m, 2H), 7.65 (m, 2H), 7.58–7.40 (m, 3H), 7.30 (m, 3H), 4.42, 4.40 (d, 1H), 3.63 (m, 1H), 2.40 (m, 2H); MS APCI Probe temperature 450° C., cone voltage 25 volts, acetonitrile:methanol 4:1, 384.4 (M+H)$^+$.

EXAMPLE 34

3-(Naphthalene-1-Sulfonylamino)-4-Oxo-Butyric Acid

Naphthalene-1-sulfonyl chloride was employed to acylate the amine of Asp(OtBu)—NMe(OMe). From the resulting sulfonamide, final product was obtained as a colorless foam (90 mg, 66%) employing methods previously described. $^1$H NMR (CD$_3$OD) as the lactol; 8.85 (m, 1H), 8.25 (t, 1H), 8.16 (t, 1H), 8.00 (d, 1H) 7.72–7.52 (m, 3H), 4.38, 4.09 (dd, 1H), 3.67 (m, 1H), 2.80–2.22 (m, 2H); MS APCI Probe temperature 450° C., cone voltage 25 volts, acetonitrile:methanol 4:1, 308.5 (M+H)$^+$.

EXAMPLE 35

3-(3'-Methyl-Biphenyl-2-Sulfonylamino)-4-Oxo-Butyric Acid

3'-Methyl-biphenyl-2-sulfonyl chloride was employed to acylate the amine of Asp(OtBu)—NMe(OMe). From the resulting sulfonamide, final product was obtained as a colorless foam (160 mg, 76%) employing methods previously described. $^1$H NMR (CD$_3$OD) as the lactol; 8.07 (m, 1H), 7.60 (m, 1H), 7.52 (m, 1H), 7.38–7.08 (m, 5H), 4.43 (m, 1H), 2.43 (m, 1H), 2.38 (s, 3H), 2.25 (m, 1H); MS APCI Probe temperature 450° C., cone voltage 25 volts, acetonitrile:methanol 4:1, 348.3 (M+H)$^+$.

EXAMPLE 36

3-[2-(Naphthalen-2-Yloxy)-Benzenesulfonylamino]-4-Oxo-Butyric Acid 2-(Naphthalen-2-yloxy)-benzenesulfonyl chloride was employed to acylate the amine of Asp(OtBu)—NMe(OMe). From the resulting sulfonamide, final product was obtained as a colorless foam (60 mg, 37%) employing methods previously described. $^1$H NMR (CD$_3$OD) as the lactol; 7.98 (m, 2H), 7.87 (m, 1H), 7.81 (m, 1H), 7.60 (m, 1H), 7.45 (m, 3H), 7.38 (m, 1H), 7.20 (m, 1H), 6.90 (m, 1H), 4.60,4.57 (d, 1H), 3.80 (m, 1H), 2.65–2.44 (m, 2H); MS APCI Probe temperature 450° C., cone voltage 25 volts, acetonitrile:methanol 4:1, 399.8 (M+H)$^+$.

EXAMPLE 37

3-(6-Methyl-Biphenyl-2-Sulfonylamino)-4-Oxo-Butyric Acid

6-Methyl-biphenyl-2-sulfonyl chloride was employed to acylate the amine of Asp(OtBu)—NMe(OMe). From the resulting sulfonamide, final product was obtained as a colorless foam (120 mg, 86%) employing methods previously described. ¹H NMR (CD₃OD) as the lactol; 7.92 (m, 1H), 7.52 (d, 1H), 7.40 (m, 4H), 7.30 (t, 1H), 7.20 (t, 1H), 4.46 (d, 1H), 3.65 (m, 1H), 2.52–2.32 (m, 2H), 1.98 (s, 3H); MS APCI Probe temperature 450° C., cone voltage 25 volts, acetonitrile:methanol 4:1, 348.10 (M+H)⁺.

EXAMPLE 38

3-(3-Methyl-2-Phenoxy-Benzenesulfonylamino)-4-Oxo-Butyric Acid 2-(Phenyloxy)-3-methybenzenesulfonyl chloride was employed to acylate the amine of Asp(OtBu)—NMe(OMe). From the resulting sulfonamide, final product was obtained as a colorless foam (100 mg, 55%) employing methods previously described. ¹H NMR (CD₃OD) as the lactol; 7.82 (t, 1H), 7.53 (t, 1H), 7.32 (m, 1H), 7.25 (t, 2H), 7.02 (t, 1H), 6.81 (d, 2H), 4.52, 4.42 (d, 1H), 3.75 (m, 1H), 2.54 (m, 1H), 2.42 (m, 1H), 2.04 (s, 3H); MS APCI Probe temperature 450° C., cone voltage 25 volts, acetonitrile:methanol 4:1, 361.9 (M–H)⁻.

EXAMPLE 39

4-Oxo-3-[2-Phenylthio-Benzenesulfonylamino]-Butyric Acid

2-Phenylthio-benzenesulfonyl chloride was employed to acylate the amine of Asp(OtBu)—NMe(OMe). From the resulting sulfonamide, final product was obtained as a colorless foam (140 mg, 80%) employing methods previously described. ¹H NMR (CD₃OD) as the lactol; 7.95 (m, 1H), 7.69 (m, 1H), 7.44 (m, 2H), 7.35 (t, 1H), 7.27 (t, 1H), 7.00 (d, 1H), 4.56, 4.53 (d, 1H), 3.75 (m, 1H), 2.60 (m, 1H), 2.44 (m, 1H); MS APCI Probe temperature 450° C., cone voltage 25 volts, acetonitrile:methanol 4:1, 363.8 (M–H)⁻.

EXAMPLE 40

4-Oxo-3-[2-N-Phenyl-Benzenesulfonylamino]-Butyric Acid

2-N-phenyl-benzenesulfonyl chloride was employed to acylate the amine of Asp(OtBu)—NMe(OMe). From the resulting sulfonamide, final product was obtained as a colorless foam (25 mg, 18%) employing methods previously described. ¹H NMR (CD₃OD) as the lactol; 7.81 (m, 1H), 7.36 (m, 3H), 7.24 (m, 3H), 7.15 (t, 1H), 6.98 (t, 1H), 6.88 (t, 1H), 4.52, 4.45 (d, 1H), 3.65 (m, 1H), 2.62 (m, 1H), 2.38 (m, 1H); MS APCI Probe temperature 450° C., cone voltage 25 volts, acetonitrile:methanol 4:1, 347.0 (M–H)⁻.

EXAMPLE 41

3-[2-(4-Isopropylphenoxy)-3-Methylbenzenesulfonylamino]-4-Oxo-Butyric Acid

4-Isopropylphenyloxy-3-methybenzenesulfonyl chloride was employed to acylate the amine of Asp(OtBu)—NMe(OMe). From the resulting sulfonamide, final product was obtained as a colorless foam (110 mg, 82%) employing methods previously described. ¹H NMR (CD₃OD) as the lactol; 7.82 (t, 1H), 7.53 (t, 1H), 7.30 (m, 1H), 7.13 (d, 2H), 6.73 (d, 2H), 4.52, 4.42 (d, 1H), 3.74 (q, 1H), 2.58 (m, 1H), 2.42 (m, 1H), 2.03 (s, 3H), 1.20 (s, 6H); MS APCI Probe temperature 450° C., cone voltage 25 volts, acetonitrile:methanol 4:1, 406.1 (M+H)⁺.

EXAMPLE 42

3-[2-(2-Methylphenoxy)-3-Methylbenzenesulfonylamino]-4-Oxo-Butyric Acid

2-Methylphenyloxy-3-methybenzenesulfonyl chloride was employed to acylate the amine of Asp(OtBu)—NMe (OMe). From the resulting sulfonamide, final product was obtained as a colorless foam (150 mg, 66%) employing methods previously described. ¹H NMR (CD₃OD) as the lactol; 7.80 (m, 1H), 7.51 (m, 1H), 7.32 (m, 1H), 7.10 (t, 1H), 6.98 (t, 1H), 6.86 (m, 1H), 6.28 (m, 1H), 4.42, 4.28 (d, 1H), 3.68 (m, 1H), 2.58 (m, 1H), 2.44 (s, 3H), 2.38 (m, 1H), 1.95 (s, 3H); MS APCI Probe temperature 450° C., cone voltage 25 volts, acetonitrile:methanol 4:1,378.1 (M+H)⁺.

EXAMPLE 43

4-Oxo-3-[2-(Tetrahydro-Furan-2-Ylmethoxy)-Benzenesulfonylamino]-Butyric Acid 2-(Tetrahydro-furan-2-ylmethoxy)-benzenesulfonyl chloride was employed to acylate the amine of Asp(OtBu)—NMe(OMe). From the resulting sulfonamide, final product was obtained as a thick oil (0.1033 g, 15%) employing methods previously described. ¹H NMR (CD₃OD, ppm) as the lactol; 7.9–7.7 (m, 1H), 7.7–7.5 (m, 1H), 7.3–7.0 (m, 2H), 4.5–4.2 (m, 3H), 4.2–3.6 (m, 4H), 2.7–2.2 (m, 2H), 2.2–1.7 (m, 4H). MS APCI Probe temperature 450° C., cone voltage 25 volts, acetonitrile:methanol 4:1, 358.1 (M+H)⁺.

EXAMPLE 44

3-(5-Methyl-2-Phenoxy-Benzenesulfonylamino)-4-Oxo-Butyric Acid

5-Methyl-2-phenoxy-benzenesulfonyl chloride was employed to acylate the amine of Asp(OtBu)—NMe(OMe). From the resulting sulfonamide, final product was obtained as a pink foam (0.2274 g, 30%) employing methods previously described. ¹H NMR (CD₃OD, ppm) as the lactol; 7.73 (m, 1H), 7.5–7.0 (m, 7H), 6.76 (d, 1H), 4.5 (dd, 1H), 3.7–3.6 (m, 1H), 2.7–2.4 (m, 2H), 2.36 (s, 3H). MS APCI Probe temperature 450° C., cone voltage 25 volts, acetonitrile:methanol 4:1, 362.9 (M–H)⁻.

EXAMPLE 45

3-(4-Methyl-2-Phenoxy-Benzenesulfonylamino)-4-Oxo-Butyric Acid

4-Methyl-2-phenoxy-benzenesulfonyl chloride was employed to acylate the amine of Asp(OtBu)—NMe(OMe). From the resulting sulfonamide, final product was obtained as a colorless foam (0.1279 g, 15%) employing methods previously described. ¹H NMR (CD₃OD, ppm) as the lactol; 7.8 (m, 1H), 7.4 (m, 2H), 7.3–6.9 (m, 4H), 6.65 (s, 1H), 4.5 (dd, 1H), 3.7 (m, 1H), 2.7–2.4 (m, 2H), 2.28 (s, 3H). MS APCI Probe temperature 450° C., cone voltage 25 volts, acetonitrile:water 4:1, 364.1 (M+H)⁺.

EXAMPLE 46

3-(2-Nitro-Benzenesulfonylamino)-4-Oxo-Butyric Acid

2-Nitro-benzenesulfonyl chloride was employed to acylate the amine of Asp(OtBu)—NMe(OMe). From the resulting sulfonamide, final product was obtained as a thick yellow oil (0.028 g, 4%) employing methods previously described. ¹H NMR (CD₃OD, ppm) as the lactol; 8.11 (m, 1H), 7.88 (m, 1H), 7.79 (m, 2H), 4.50 (m, 1H), 3.83 (m, 1H), 2.7–2.4 (m, 2H). MS APCI Probe temperature 450° C., cone voltage 25 volts, acetonitrile:water 4:1, 301.9 (M)⁻.

INHIBITION STUDIES

Compounds of Formulas I, II, or III are inhibitors of ICE as demonstrated by measurement of $K_i$ ($\mu$M) and $IC_{50}$ ($\mu$M)

using the protocol described herein. ICE (0.24 nM final concentration) is added to 400 μL of HGDE buffer (100 mM HEPES, 20% glycerol, 5 mM DTT, 0.5 mM EDTA) containing 15 μM substrate (Ac—Tyr—Val—Ala—Asp—AMC; $K_M$=15 μM) plus vehicle (DMSO) or inhibitor at concentrations bracketing the $K_i$. Substrate hydrolysis is monitored for 300 seconds by observing the fluorescence of released AMC using excitation at 380 nm and emission at 460 nm. Mean rates of substrate hydrolysis are evaluated by linear-regression analysis of the fluorescence vs time traces. To evaluate $K_i$, plots of percent inhibition vs inhibitor concentration are fit by non-linear regression to a reversible, competitive model:

$$\% \text{ Inhibition} = \frac{100*[I]}{[I]+Ki*\left(1+\frac{[S]}{KM}\right)}$$

where the competition factor $(1+[S]/K_M)=2$.

ICE Colorimetric Dose-Response (IC$_{50}$) Assay

Diluted inhibitor stocks are prepared by two-fold serial dilution from a primary stock whose concentration is selected (based on screening results or on prior attempts at IC$_{50}$ evaluation) to achieve approximately 95% inhibition in the most concentrated well. Aliquots of each dilution are transferred to a microtitre plate in triplicate.

ICE enzyme is diluted to approximately 24 nM in HGE buffer (100 mM Hepes pH 7.5, 0.5 mM EDTA, 20% glycerol, 0.1% Bovine Serum Albumin (BSA), and activated by adding dithiothreitol (DTT) to a final concentration of 5 mM. The activated enzyme is then aliquoted into wells containing inhibitor or vehicle, and the plate is preincubated for 60 minutes at ambient temperature. Substrate (Ac—Tyr—Val—Ala—Asp—pNA) is added to each well to a final concentration of 50 μM, and plates are placed in the microtitre plate-reader thermostated to 25° C. Beginning 5 minutes after addition of substrate, absorbance (405 nm) of wells is monitored for 1 hour, and activity is calculated as the mean rate of change in absorbance during this interval.

PBMC Cellular Assay (IC$_{50}$) Determinations

Further evidence that compounds of Formula I, II, and III are inhibitors of ICE is provided by their ability to inhibit IL-1β production in human peripheral blood mononuclear cells (PBMCs) as described herein. PBMCs are isolated from heparinized blood by centrifugation over a ficoll cushion, then washed three times with phosphate-buffered saline. PBMCs are suspended in a medium containing RPMI 1640 with glutamine, penicillin, streptomycin, and 2% human AB serum, then plated at 10$^6$ cells per well in 96 well flat bottom plates. PBMCs are stimulated overnight with 10 ng/mL of lipopolysaccharide (LPS, *E. Coli* strain 0111:B4; Calbiochem) in the presence or absence of a compound of Formula I. Medium is harvested and the level of mature IL-1β was determined using an ELISA kit from R & D Systems. Compound inhibition is assessed by determining the concentration of agent which reduces IL-1β levels by 50%. Cells were cultured for an additional four hours in the presence of 3-(4,5-dimethylthiazol-2-yl)-2,5-diphenyltetrazolium bromide (MTT) to determine viability. Compound toxicity can, therefore, be assessed by determining the concentration of agent which kills 50% of the cells (IC$_{50}$).

Ich-2 (Caspase-4) Colorimetric Dose-Response (IC$_{50}$) Assay

Inhibition of Ich-2 enzyme is assayed as described above for ICE, except that enzyme is used at 64 nM, and 60 μM of the Ich-2-specific substrate Ac—Leu—Glu—Val—Asp—pNA is used instead of the ICE substrate Ac—Tyr—Val—Ala—Asp—pNA. The results of these test are shown below in Table 1.

TABLE 1

| Example Number | ICE $K_i$ (μM) | ICE IC$_{50}$ (μM) | PBMC IC$_{50}$ (μM) | PBMC TC$_{50}$ (μM) | Ich-2 (Caspase-4) IC$_{50}$ (μM) |
|---|---|---|---|---|---|
| 1 | 1.6 | 20.3 | >100 | >100 | 88 |
| 2 | 6.8 | 86.8 | >100 | ND | 259 |
| 3 | 3.7 | 37.0 | ND | ND | 70 |
| 4 | 2.4 | 24.0 | ND | ND | 52 |
| 5 | 1.1 | 8.8 | 67.5 | >100 | 18 |
| 6 | 0.54 | 5.3 | 23.5 | >100 | 6.1 |
| 7 | 0.43 | 10.8 | 67.5 | >100 | 33 |
| 8 | 0.41 | 3.7 | 45.0 | >100 | 6.1 |
| 9 | 6.4 | 66.2 | ND | ND | 109 |
| 10 | 4.2 | 22 | 90 | >100 | 318 |
| 11 | 17 | 55 | ND | ND | 569 |
| 12 | 3 | 14 | 90 | >100 | 59 |
| 13 | 7 | 32 | ND | ND | 167 |
| 14 | 2.3 | 20 | 90 | >100 | 35 |
| 15 | 1 | 5.1 | 50 | >100 | 22 |
| 16 | 1.3 | 5.8 | 65 | >100 | 42 |
| 17 | 0.9 | 9.2 | 55 | >100 | 63 |
| 18 | 2 | 14 | 80 | >100 | 87 |
| 19 | 0.5 | 2.2 | 23 | >100 | 4.0 |
| 20 | 0.3 | 4.4 | 40 | >100 | 17 |
| 21 | 0.6 | 6.1 | 33 | 70 | 31 |
| 22 | 0.11 | 1.0 | 25 | >100 | 76 |
| 23 | 0.8 | 11 | 60 | >100 | 97 |
| 24 | 1.0 | 13 | 73 | >100 | 122 |
| 25 | 0.44 | 3.5 | 27 | >100 | 6.5 |
| 26 | 0.45 | 7.8 | 58 | >100 | 23 |
| 27 | 3.9 | 35 | >100 | >100 | 118 |
| 28 | 0.1 | 1.0 | 18 | >100 | 4.6 |
| 29 | 0.3 | 8.6 | 75 | >100 | 215 |
| 30 | 4.2 | 37 | ND | ND | 221 |
| 31 | 0.062 | 0.40 | 8.0 | >100 | 2.3 |
| 32 | 7 | 28 | ND | ND | 603 |
| 33 | 7 | 11.4 | ND | ND | 77 |
| 34 | 31 | 110 | ND | ND | 602 |
| 35 | 31 | 37 | >100 | >100 | 341 |
| 36 | 0.13 | 3.5 | 50 | >100 | 28 |
| 37 | 1.9 | 34 | >100 | >100 | 151 |
| 38 | 0.67 | 11.2 | 85 | >100 | 76 |
| 39 | 1.1 | 21 | >100 | >100 | 25 |
| 40 | 10 | 44 | 95 | >100 | 370 |
| 41 | 1.5 | 12 | 45 | >100 | 9.2 |
| 42 | 0.30 | 1.1 | 38 | >100 | 57 |
| 43 | 7.7 | 99 | ND | ND | 1,973 |
| 44 | 2.2 | 41 | >100 | >100 | 199 |
| 45 | 18 | 1.7 | 70 | >100 | 14 |
| 46 | 10 | 130 | ND | ND | 525 |

ND = Not determined
HEPES = 4-(2-hydroxymethyl)-1-piperazine ethane sulfonic acid
DTT = Dithiothreitol
EDTA = Ethylene diamine tetra acetic acid
AMC = 7-amino-4-methyl coumarin
Tyr = Tyrosine
Val = Valine
Ala = Alanine
Asp = Aspartic Acid
pNA = Para nitroaniline
LEU = Leucine
Glu = Glutamic acid
tBu = tert-butyl
Me = Methyl
APCI = Atmospheric pressure chemical ionization

What is claimed is:

1. A compound having the Formula I

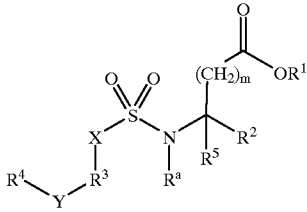

wherein $R^1$ is hydrogen, $C_1$–$C_6$alkyl, or benzyl;

$R^2$ is —CHO, —COR$^a$, or —CN;

each $R^a$ is independently hydrogen or $C_1$–$C_6$alkyl;

X is a bond, $CH_2$, $CHR^5$, NH, $NR^5$, or O;

$R^3$ is aryl, substituted-aryl, heteroaryl, substituted-heteroaryl, cycloalkyl, substituted-cycloalkyl, heterocycle, or substituted heterocycle;

Y is absent, $NR^5$, CO, S, O, $SO_2$, —O(CHR$^5$)$_n$—, CHR$^5$, NR$^5$CO,

CONR$^5$, OCHR$^5$, CHR$^5$O, SCHR$^5$, CHR$^5$S, SO$_2$NR$^5$, $C_1$—$C_6$alkyl, NR$^5$SO$_2$, CH$_2$CHR$^5$CHR$^5$CH$_2$COCH$_2$, or CH$_2$CO;

$R^4$ is absent, aryl, substituted-aryl, $C_1$–$C_8$alkyl, heteroaryl, substituted-heteroaryl, cycloalkyl, $C_1$–$C_6$alkyl, substituted-cycloalkyl, heterocycloalkyl, or substituted heterocycloalkyl;

each $R^5$ is independently hydrogen, $C_1$–$C_6$alkyl, aryl, —(CH$_2$)$_n$aryl, or —(CH$_2$)$_n$cycloalkyl;

each n is independently 0 to 5, m is 1 or 2, and the pharmaceutically acceptable salts and amides thereof.

2. The compound according to claim 1 wherein $R^2$ is CHO.

3. The compound according to claim 1 wherein $R^1$ is hydrogen.

4. The compound according to claim 1 wherein $R^a$ is hydrogen.

5. The compound according to claim 1 wherein X is a bond.

6. The compound according to claim 1 wherein $R^3$ is phenyl or substituted phenyl.

7. The compound according to claim 1 wherein Y is a bond.

8. The compound according to claim 1 wherein Y is O.

9. The compound according to claim 1 wherein Y is CH$_2$.

10. The compound according to claim 1 wherein $R^4$ is phenyl or substituted phenyl.

11. The compound according to claim 1 wherein $R^2$ is CHO, $R^a$ is H, $R^1$ is hydrogen, X is a bond, $R^3$ and $R^4$ are phenyl or substituted phenyl, and Y is a bond, CH$_2$, or O.

12. The compound according to claim 1 wherein m is 1 and $R^5$ is hydrogen.

13. A compound of Formula II

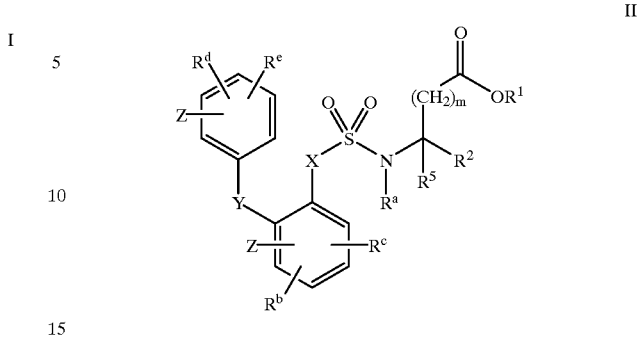

wherein $R^1$ is hydrogen, $C_1$–$C_6$alkyl, or benzyl;

$R^2$ is —CHO, —COR$^a$, or —CN;

each $R^a$ is independently hydrogen or $C_1$–$C_6$alkyl;

X is a bond, CH$_2$, CHR$^5$, NH, NR$^5$, or O;

Y is a bond, NR$^5$, CO, S, O, SO$_2$, CHR$^5$, NR$^5$CO, CONR$^5$, OCHR$^5$, —O(CHR$^5$)$_n$—, CHR$^5$O, SCHR$^5$, CHR$^5$S, SO$_2$NR$^5$, NR$^5$SO$_2$, CH$_2$CHR$^5$, CHR$^5$CH$_2$, COCH$_2$, or CH$_2$CO;

each $R^5$ is independently hydrogen, $C_1$–$C_6$alkyl, aryl, or —(CH$_2$)$_n$aryl;

each n is independently 0 to 5;

m is 1 or 2;

Each Z is independently hydrogen, or an aryl, substituted aryl, heteroaryl, substituted heteroaryl, cycloalkyl, substituted cycloalkyl, heterocycle, or substituted heterocycle group that is fused to the phenyl group that contains Z as a substituent;

$R^b$, $R^c$, $R^d$, and $R^e$ are each independently hydrogen, $C_1$–$C_6$alkyl, $C_1$–$C_6$alkoxy, —OH, $C_1$–$C_6$thioalkoxy, halogen, trifluoromethyl, dialkylamino, —NO$_2$, —CN, —CF$_3$, —CO$_2$alkyl, —SO$_3$H, —CHO, —COalkyl, —CONH-alkyl, —CONHR$^q$, —CON(alkyl)$_2$, —(CH$_2$)$_n$—NH$_2$, —(CH$_2$)$_n$—NH-alkyl, —NHR$^q$, —NHCOR$^q$, —(CH$_2$)$_n$OH, —(CH$_2$)$_n$CONH$_2$, or —(CH$_2$)$_n$CO$_2$H; and $R^q$ is hydrogen or $C_1$–$C_6$alkyl, and the pharmaceutically acceptable salts, amides thereof.

14. The compound according to claim 13 wherein $R^1$ is hydrogen.

15. The compound according to claim 13 wherein $R^2$ is CHO.

16. The compound according to claim 13 wherein $R^a$ is hydrogen.

17. The compound according to claim 13 wherein X is a bond.

18. The compound according to claim 13 wherein Y is a bond, O, or CH$_2$.

19. The compound according to claim 13 wherein $R^b$ and $R^c$ are hydrogen.

20. The compound according to claim 13 wherein $R^b$, $R^c$, and $R^d$ are hydrogen and $R^e$ is $C_1$–$C_6$alkyl.

21. The compound according to claim 13 wherein $R^b$ or $R^c$ is located at the para position of the phenyl ring with respect to X and $R^b$ or $R^c$ is —OCH$_3$.

22. The compound according to claim 13 wherein is 1 and $R^5$ is hydrogen.

23. The compound selected from the group consisting of 3-(Biphenyl-2-sulfoamino)-4-oxo-butyric acid;

3-(2-Benzyl-benzenesulfonylamino)-4-oxo-butyric acid;

4-Oxo-3-(2-phenoxy-benzenesulfonylamino)-butyric acid;

4-Oxo-3-(2-p-tolyloxy-benzenesulfonylamino)-butyric acid;

3-[2-(4-Isopropyl-phenoxy)-benzenesulfonylamino]-4oxo-butyric acid;

4-Oxo-3-(2-m-tolyloxy-benzenesulfonylamino)-butyric acid;

3-[2-(3-Isopropyl-phenoxy)-benzenesulfonylamino]-4-oxo-butyric acid; and 3-(4'-Methyl-biphenyl-2-sulfonylamino)-4-oxo-butyric acid.

24. The compound of the Formula III

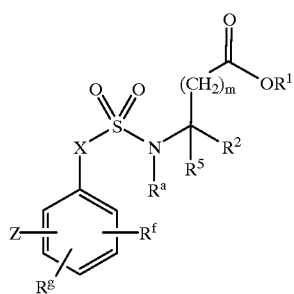

wherein $R^1$ is hydrogen, $C_1$–$C_6$alkyl, or benzyl;

$R^2$ is —CHO, —COR$^a$, or —CN;

each $R^a$ is independently hydrogen or $C_1$–$C_6$alkyl;

X is a bond, $CH_2$, $CHR^5$, NH, $NR^5$, or O;

$R^5$ is hydrogen, $C_1$–$C_6$alkyl, aryl, or —$(CH_2)_n$aryl;

each n is independently 0 to 5;

m is 1 or 2;

Z is absent, or an aryl, substituted aryl, heteroaryl, substituted heteroaryl, cycloalkyl, substituted cycloalkyl, heterocycle, or substituted heterocycle group that is fused to the phenyl group that contains Z as a substituent;

$R^f$, $R^g$, are each independently hydrogen, $C_1$–$C_6$alkyl, hydroxy, halogen, trifluoromethyl, dialkylamino, —$NO_2$, —CN, —$CO_2H$, —$CO_2$alkyl, —$SO_3H$, —CHO, —COalkyl, —$CONH_2$, —$CONH(CH_2)_n$aryl, —$CONH(CH_2)_n$-substituted-aryl, —CONH-alkyl, —CONHR$^q$, —CON(alkyl)$_2$, —$(CH_2)_n$—$NH_2$, —$(CH_2)_n$—NH-alkyl, —NHR$^q$, —NHCOR$^q$, —OR$^q$, —SR$^q$, or —$(CH_2)_n$aryl; and $R^q$ is hydrogen or $C_1$–$C_8$alkyl, and the pharmaceutically acceptable salts and amides thereof.

25. The compound in accordance with claim 24 wherein $R^f$ is ortho to X on the phenyl ring and $R^g$ is hydrogen.

26. The compound in accordance with claim 24 wherein Z is hydrogen, m is 1, $R^5$ is hydrogen, and $R^9$ is hydrogen.

27. The compound 3-benzenesulfonylamino-4-oxo-butyric acid.

28. A method of inhibiting interleukin-1β converting enzyme, the method comprising administering to a patient in need thereof a therapeutically effective amount of a compound of claim 1.

29. A method of inhibiting interleukin-1β converting enzyme, the method comprising administering to a patient in need thereof a therapeutically effective amount of a compound of claim 24.

30. A method of inhibiting Caspase-4, the method comprising administering to a patient in need thereof a Caspase-4 inhibiting amount of a compound of claim 1.

31. A method of inhibiting Caspase-4, the method comprising administering to a patient in need thereof a Caspase-4 inhibiting amount of a compound of claim 24.

32. A method of treating stroke, the method comprising administering to a patient having a stroke or having had a stroke a therapeutically effective amount of a compound of claim 1.

33. A method of treating stroke, the method comprising administering to a patient having a stroke or having had a stroke a therapeutically effective amount of a compound of claim 24.

34. A method of treating inflammatory diseases, the method comprising administering to a patient having an inflammatory disease a therapeutically effective amount of a compound of claim 1.

35. A method of treating inflammatory diseases, the method comprising administering to a patient having an inflammatory disease a therapeutically effective amount of a compound of claim 24.

36. The method of claim 34 wherein the inflammatory disease is arthritis or inflammatory bowel disease.

37. The method of claim 35 wherein the inflammatory disease is arthritis or inflammatory bowel disease.

38. A method of treating septic shock, the method comprising administering to a patient having septic shock a therapeutically effective amount of a compound of claim 1.

39. A method of treating septic shock, the method comprising administering to a patient having septic shock a therapeutically effective amount of a compound of claim 24.

40. A method of treating reperfusion injury, the method comprising administering to a patient in need thereof a therapeutically effective amount of a compound of claim 1.

41. A method of treating reperfusion injury, the method comprising administering to a patient in need thereof a therapeutically effective amount of a compound of claim 24.

42. A method of treating Alzheimer's disease, the method comprising administering to a patient having Alzheimer's disease a therapeutically effective amount of a compound of claim 1.

43. A method of treating Alzheimer's disease, the method comprising administering to a patient having Alzheimer's disease a therapeutically effective amount of a compound of claim 24.

44. A method of treating shigellosis, the method comprising administering to a patient having shigellosis a therapeutically effective amount of a compound of claim 1.

45. A method of treating shigellosis, the method comprising administering to a patient having shigellosis a therapeutically effective amount of a compound of claim 24.

46. A pharmaceutically acceptable composition comprising a compound of claim 1 and a pharmaceutically acceptable carrier thereof.

47. A pharmaceutically acceptable composition comprising a compound of claim 24 and a pharmaceutically acceptable carrier thereof.

48. The compound selected from the group consisting of 3-(2-Isobutoxy-benzenesulfonylamino)-4-oxo-butyric acid;

3-[2-(2-Methyl-pentanoylamino)-benzenesulfonylamino]-4-oxo-butyric acid;

4-Oxo-3-(2-o-tolyloxy-benzenesulfonylamino)-butyric acid;

4-Oxo-3-(2-phenethyl-benzenesulfonylamino)-butyric acid;

3-(2-Cyclohexyloxy-benzenesulfonylamino)-4-oxo-butyric acid;

3-[2-(1-Chloro-naphthalen-2-yloxy)-benzenesulfonylamino]-4-oxo-butyric acid;

4-Oxo-3-[2-(5,6,7,8-tetrahydro-naphthalen-2-yloxy)-benzenesulfonylamino]-butyric acid;

4-Oxo-3-(2-phenethyloxy-benzenesulfonylamino)-butyric acid;

3-[2-(2-Ethyl-phenoxy)-benzenesulfonylamino]-4-oxo-butyric acid;

3-[2-(4-sec-Butyl-phenoxy)-benzenesulfonylamino]-4-oxo-butyric acid;

3-[2-(Biphenyl-4-yloxy)-benzenesulfonylamino]-4-oxo-butyric acid;

3-{2-[4-(1-Methyl-pentyl)-phenoxy]-benzenesulfonylamino}-4-oxo-butyric acid;

3-[2-(4-Isopropyl-3-methyl-phenoxy)-benzenesulfonylamino]-4-oxo-butyric acid;

3-(2-Benzyloxy-benzenesulfonylamino)-4-oxo-butyric acid;

3-[2-(2,3-Dimethyl-phenoxy)-benzenesulfonylamino]-4-oxo-butyric acid;

3-{2-[4-(1-Ethyl-propyl)-phenoxy]-benzenesulfonylamino}-4-oxo-butyric acid;

4-Oxo-3-[2-(3,4,5-trimethyl-phenoxy)-benzenesulfonylamino]-butyric acid;

3-(2-sec-Butoxy-benzenesulfonylamino)-4-oxo-butyric acid;

3-[2-(4-sec-Butyl-3-methyl-phenoxy)-benzenesulfonylamino]-4-oxo-butyric acid;

3-(2-Ethylbutoxy-benzenesulfonylamino)-4-oxo-butyric acid;

3-(2-Methylbutoxy-benzenesulfonylamino)-4-oxo-butyric acid;

4-Oxo-3-[2-(1-naphthyl)ethyloxy]-benzenesulfonylamino)-butyric acid;

3-(2'-Methyl-biphenyl-2-sulfonylamino)-4-oxo-butyric acid;

3-(2-Naphthalen-1-yl-benzenesulfonylamino)-4-oxo-butyric acid;

3-(Naphthalene-1-sulfonylamino)-4-oxo-butyric acid;

3-(3'-Methyl-biphenyl-2-sulfonylamino)-4-oxo-butyric acid;

3-[2-(Naphthalen-2-yloxy)-benzenesulfonylamino]-4-oxo-butyric acid;

3-(6-Methyl-biphenyl-2-sulfonylamino)-4-oxo-butyric acid;

3-(3-Methyl-2-phenoxy-benzenesulfonylamino)-4-oxo-butyric acid;

4-Oxo-3-[2-phenylthio-benzenesulfonylamino]-butyric acid;

4-Oxo-3-[2-N-phenyl-benzenesulfonylamino]-butyric acid;

3-[2-(4-Isopropylphenoxy)-3-methylbenzenesulfonylamino]-4-oxo-butyric acid;

3-[2-(2-Methylphenoxy)-3-methylbenzenesulfonylamino]-4-oxo-butyric acid;

4-Oxo-3-[2-(tetrahydro-furan-2-ylmethoxy)-benzenesulfonylamino]-butyric acid;

3-(5-Methyl-2-phenoxy-benzenesulfonylamino)-4-oxo-butyric acid;

3-(4-Methyl-2-phenoxy-benzenesulfonylamino)-4-oxo-butyric acid; and 3-(2-Nitro-benzenesulfonylamino)-4-oxo-butyric acid.

* * * * *